(12) United States Patent
Huang et al.

(10) Patent No.: US 10,806,584 B2
(45) Date of Patent: Oct. 20, 2020

(54) OSTEO-IMPLANT

(71) Applicants: Industrial Technology Research Institute, Hsinchu (TW); National Taiwan University Hospital, Taipei (TW)

(72) Inventors: Chih-Chieh Huang, Miaoli County (TW); Pei-I Tsai, Hsinchu (TW); Hsin-Hsin Shen, Hsinchu County (TW); Yi-Hung Wen, Hsinchu (TW); Kuo-Yi Yang, Hsinchu (TW); Wei-Luan Fan, Miaoli County (TW); Jui-Sheng Sun, Taipei (TW); Nien-Ti Tsou, Taipei (TW)

(73) Assignees: Industrial Technology Research Institute, Hsinchu (TW); National Taiwan University Hospital, Taipei (TW)

( * ) Notice: Subject to any disclaimer, the term of this patent is extended or adjusted under 35 U.S.C. 154(b) by 761 days.

(21) Appl. No.: 15/393,252

(22) Filed: Dec. 29, 2016

(65) Prior Publication Data
US 2018/0177596 A1  Jun. 28, 2018

(30) Foreign Application Priority Data
Dec. 28, 2016 (TW) .............................. 105143553 A

(51) Int. Cl.
*A61B 17/86* (2006.01)
*A61F 2/28* (2006.01)
(Continued)

(52) U.S. Cl.
CPC ............ *A61F 2/28* (2013.01); *A61B 17/7035* (2013.01); *A61B 17/863* (2013.01);
(Continued)

(58) Field of Classification Search
CPC .......... A61F 2/28; A61F 2/32; A61F 2/30771; A61F 2002/2817; A61F 2002/285;
(Continued)

(56) References Cited

U.S. PATENT DOCUMENTS 5,823,777 A    10/1998  Misch et al.
5,891,146 A *   4/1999  Simon .................. A61B 17/863
                                              411/414

(Continued)

FOREIGN PATENT DOCUMENTS

CN    201409989    2/2010
CN    204931870    1/2016
(Continued)

OTHER PUBLICATIONS

"Notice of Allowance of Taiwan Counterpart Application," dated Dec. 14, 2017, p. 1-p. 5.
(Continued)

*Primary Examiner* — Suba Ganesan
*Assistant Examiner* — Aren Patel
(74) *Attorney, Agent, or Firm* — JCIPRNET

(57) ABSTRACT

An osteo-implant is provided, having a fixing segment and an implant end. The fixing segment is provided with a thread and at least one bone healing chamber. The bone healing chamber is located at a thread root of the thread. The bone healing chamber is a chamber inwardly depressed from a surface of the fixing segment. The fixing segment has a central axis. In the same section of the fixing segment, an area of a section, which is parallel to and passes through the central axis, of the at least one bone healing chamber closer to the implant end is smaller.

11 Claims, 7 Drawing Sheets

(51) Int. Cl.
*A61C 8/02* (2006.01)
*A61C 8/00* (2006.01)
*A61B 17/70* (2006.01)
*A61F 2/30* (2006.01)
*A61F 2/32* (2006.01)

(52) U.S. Cl.
CPC ........ *A61B 17/8625* (2013.01); *A61C 8/0006* (2013.01); *A61C 8/0022* (2013.01); *A61C 8/0045* (2013.01); *A61F 2/30771* (2013.01); *A61F 2/32* (2013.01); *A61B 17/7032* (2013.01); *A61C 2008/0046* (2013.01); *A61F 2002/2817* (2013.01); *A61F 2002/3092* (2013.01); *A61F 2002/30861* (2013.01)

(58) Field of Classification Search
CPC ..... A61C 8/0006; A61C 8/008; A61C 8/0028; A61C 2008/0046; A61B 17/825; A61B 17/83
USPC ................ 623/23.63; 433/173, 174
See application file for complete search history.

(56) References Cited

U.S. PATENT DOCUMENTS

| | | | |
|---|---|---|---|
| 6,102,703 A | 8/2000 | Day | |
| 7,156,879 B1 | 1/2007 | Albrektsson et al. | |
| 8,562,344 B2 | 10/2013 | Grant | |
| 8,979,911 B2 | 3/2015 | Martineau et al. | |
| 9,173,692 B1 | 11/2015 | Kaloostian | |
| 9,326,801 B2 | 5/2016 | Poulos | |
| 9,351,813 B1 | 5/2016 | Lyren | |
| 9,387,028 B2 | 7/2016 | Olson et al. | |
| 2004/0147929 A1 | 7/2004 | Biedermann et al. | |
| 2005/0079469 A1* | 4/2005 | Akagawa | A61C 8/0006 433/173 |
| 2008/0288076 A1 | 11/2008 | Soo et al. | |
| 2009/0191508 A1 | 7/2009 | Choi et al. | |
| 2011/0144766 A1* | 6/2011 | Kale | A61B 17/686 623/23.63 |
| 2011/0281236 A1 | 11/2011 | Onea | |
| 2013/0273500 A1* | 10/2013 | Giorno | A61C 8/0024 433/174 |
| 2017/0027669 A1* | 2/2017 | Baruc | A61C 8/0024 |
| 2019/0076257 A1* | 3/2019 | Dee | A61B 17/1635 |

FOREIGN PATENT DOCUMENTS

| | | |
|---|---|---|
| TW | M424137 | 3/2012 |
| TW | 201517880 | 5/2015 |
| TW | 201519874 | 6/2015 |
| WO | 2007074498 | 7/2007 |
| WO | 2011039162 | 4/2011 |

OTHER PUBLICATIONS

"Search Report of Europe Counterpart Application," dated Aug. 11, 2017, p. 1-p. 10.
"Office Action of China Counterpart Application", dated Jan. 19, 2020, pp. 1-9.

* cited by examiner

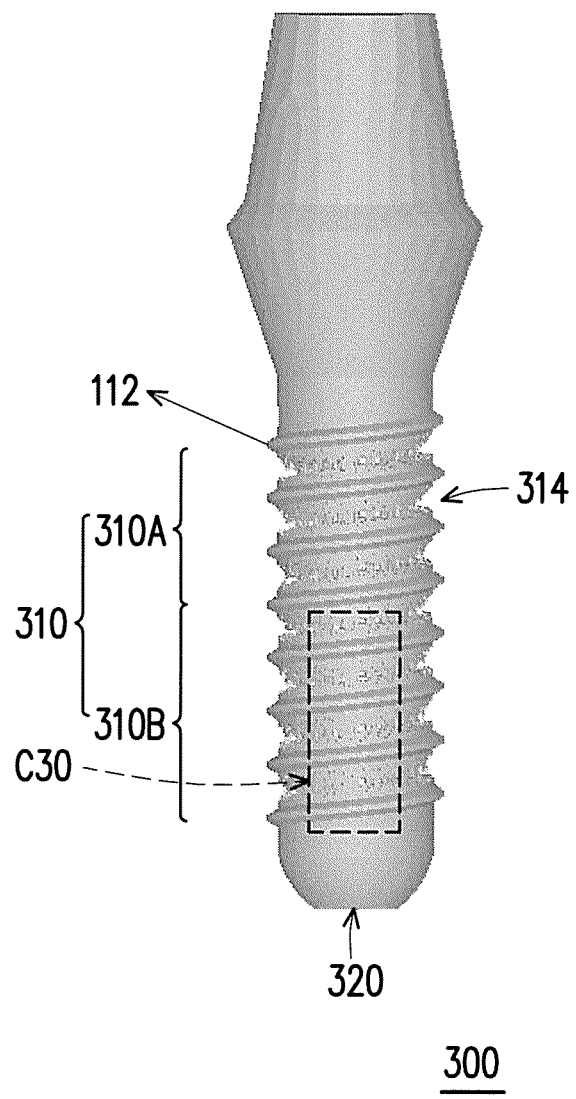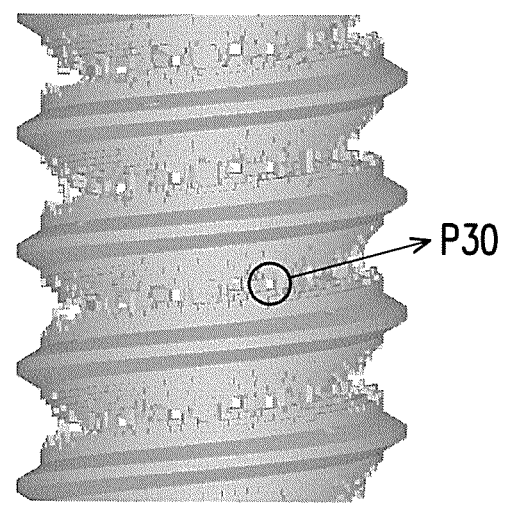
FIG. 3A
FIG. 3B

OSTEO-IMPLANT

CROSS-REFERENCE TO RELATED APPLICATION

This application claims the priority benefit of Taiwan application serial no. 105143553, filed on Dec. 28, 2016. The entirety of the above-mentioned patent application is hereby incorporated by reference herein and made a part of this specification.

TECHNICAL FIELD

The technical field relates to an implant, and in particular, to an osteo-implant.

BACKGROUND

When a bone screw or an artificial dental implant is planted in an organism, pressure may be imposed on a surrounding tissue, causing different influences. In recent years, parameterization is used to design the bone screw or the artificial dental implant, and in combination with the finite element method, the optimized bone screw or artificial dental implant is desired to be obtained. As the optimized design may be obtained only if all the possible parameters are designed with this method, and in this process, too much time is spent. However, a bone condition and a bite force of an alveolar bone of different patients are all not the same, an unfit bone screw or artificial dental implant may largely reduce the bone integration ratio, and then derives a higher rate of surgical failure, and further increases the patients' burden.

If, in a mode of matching the human bone growth, a bone screw or an artificial dental implant, which may be directly applied to all sizes, bones or bite forces of the alveolar bone, is designed, the abundant time needed by a parameterization design may be avoided, and the bone screw or the artificial dental implant fitting the patient is obtained, which may enhance the bone integration ratio effectively, to improve the success rate of tooth implantation surgery, and further reduce the patient's burden.

SUMMARY

An osteo-implant of the present disclosure has a fixing segment and an implant end. The fixing segment is provided with a thread and at least one bone healing chamber. The bone healing chamber is located at a thread root of the thread. The bone healing chamber is a chamber inwardly depressed from a surface of the fixing segment. The fixing segment has a central axis. In the same segment of the fixing segment, an area of a section, which is parallel to and passes through the central axis, of the at least one bone healing chamber closer to the implant end is smaller.

Based on the above, a section area of a bone healing chamber of the osteo-implant of the present disclosure decreases gradually towards the implant end. This design may accelerate a bone healing rate.

In order to make the above features and advantages of the present disclosure more comprehensible, detailed description is given below with embodiments and with reference to the accompanying drawings.

BRIEF DESCRIPTION OF THE DRAWINGS

FIG. 3A is a three-dimensional view of an osteo-implant in accordance with another embodiment of the present disclosure;

FIG. 3B is a local enlarged view of the osteo-implant of FIG. 3A;

DETAILED DESCRIPTION OF DISCLOSED EMBODIMENTS

Bone growth requires a proper stress, and an excessive one and an insufficient one both have bad influences. When an osteo-implant is implanted into a bone tissue, the bone tissue may produce different reactions according to different forces. When the bone bears a relatively less force, part of a trabecular bone and an inner compact bone may be removed to decrease the bone strength. When the bone bears a slightly greater force, the bone strength may be promoted. When the force borne by the bone is greater and slightly exceeds the load, the bone may be recovered healthily. When the force borne by the bone exceeds the load far, the bone may be destroyed and cannot be repaired. According to the above principles, the inventor analyzes and calculates whether each space unit fits the bone growth. A space unit fitting the bone growth may be set as a chamber left for the bone growth, and a space unit not fitting the bone growth is then set to be occupied by the osteo-implant. By the above design process, a proper shape of the osteo-implant is finally obtained. A space occupied by the material of the osteo-implant is included, for ensuring enough supporting strength, and also includes at least one bone healing chamber for recovery and growth of the bone tissue. Therefore, the inventor acquires a proper shape of the osteo-implant combining a bone ingrowth proportion and a surrounding healthy bone proportion. Several embodiments of the osteo-implant of the present disclosure are described with reference to the drawings in the following.

Figures 1A, 1B:
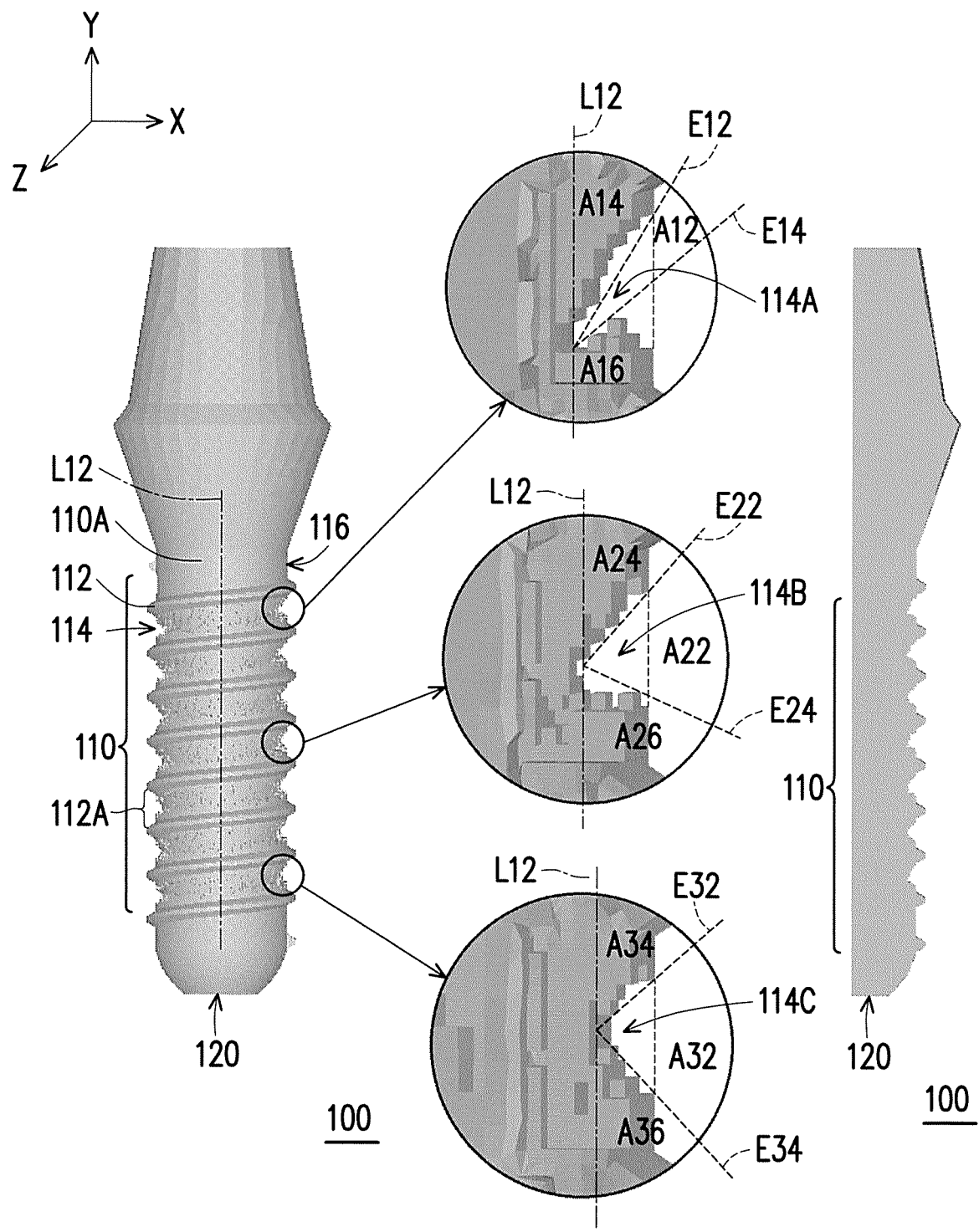
FIG. 1A is a three-dimensional view of an osteo-implant in accordance with an embodiment of the present disclosure and a local section enlarge view thereof.
FIG. 1B is a local sectional view of the osteo-implant of FIG. 1A.

FIG. 1A is a three-dimensional view of an osteo-implant in accordance with an embodiment of the present disclosure and a local section enlarge view thereof. Referring to FIG. 1A, the osteo-implant 100 of this embodiment has a fixing segment 110 and an implant end 120. The fixing segment 110 is provided with a thread 112 and at least one bone healing chamber 114. The bone healing chamber 114 is located at a thread root 112A of the thread 112. The thread 112 of this embodiment is a ridge structure of single strip, inclined to surround a surface 116 of the fixing segment 110, to enable the fixing segment 110 to be tightly bonded with the bone. However, in other embodiments, the thread may be a ridge structure of multiple strips, inclined to surround the surface of the fixing segment and parallel to each other, the thread may also be multiple closed ring-like ridge structures surrounding the surface of the fixing segment, or the thread may also be other structures that may tightly bond the fixing segment with the bone. The bone healing chamber 114 of this embodiment is in the form of a single strip, and is located at the thread root 112A of the thread 112 in a way of being parallel to the thread 112 and inclined to surround the surface 116 of the fixing segment 110. However, in other embodiments, there may also be multiple bone healing chambers 114. In addition, the bone healing chambers 114, after being added up, is, for example, substantially similar to, for example, the bone healing chamber 114 of FIG. 1A, but the bone healing chambers 114 may be separated from each other.

The bone healing chamber 114 is a chamber inwardly depressed from the surface 116 of the fixing segment 110. For example, in a separation manner, the fixing segment 110 may be divided into a columnar body 110A and the thread 112. The surface of the columnar body 110A is the surface 116 of the fixing segment 110, the thread 112 surrounds the surface 116 of the columnar body 110, and the thread root 112A is also located on the surface of the columnar body 110A. If the bone healing chamber 114 has not been formed, the original position of the surface 116 of the columnar body 110A may be indicated by a dash line of FIG. 1A. A chamber formed by depressing from the position indicated by the dash line of FIG. 1A to the interior of the osteo-implant 100 is the bone healing chamber 114. Compared with a conventional osteo-implant with a thread, the osteo-implant 100 of this embodiment has the bone healing chamber 114 depressed at the thread root 112A of the thread 112.

The fixing segment 110 has a central axis L12, and the central axis L12 is parallel to the Y axis in FIG. 1A and extends along the axial direction of the columnar body 110A. If the bone healing chamber 114 is sliced by a section parallel to and passing through the central axis L12, many sections of the bone healing chamber 114 may be obtained. In the same segment of the fixing segment 110, an area of a section of the bone healing chamber 114 closer to the implant end 120 is smaller. From another perspective, the volume of a segment of the bone healing chamber 114 closer to the implant end 120 is smaller. In this embodiment, the same segment indicates that the radius of the fixing segment 110 in the segment does not change drastically. For example, a section 114A of the bone healing chamber is farthest from the implant end 120, a section 114C of the bone healing chamber is closest to the implant end 120, and the position of a section 114B of the bone healing chamber is between the section 114A of the bone healing chamber and the section 114C of the bone healing chamber. Therefore, the area of the section 114A of the bone healing chamber is greater than that of the section 114B of the bone healing chamber, while the area of the section 114B of the bone healing chamber is greater than that of the section 114C of the bone healing chamber. As shown by the following Table 1, seven sections of the bone healing chamber 114 in FIG. 1A are numbered from being far from the implant end 120 to being close to the implant end 120, which are sequentially numbered R1-R7. If the area of the section 114A of the bone healing chamber 114 numbered R1 is 100%, it can be found that the area of the section of the bone healing chamber 114 is indeed smaller when the section is closer to the implant end 120. The area of the section 114C of the bone healing chamber which is closest to the implant end 120 and numbered R7 is merely 59.2% of the area of the section 114A of the bone healing chamber numbered R1.

TABLE 1

| Section number | Area variation of chamber section |
|---|---|
| R1 | 100% |
| R2 | 96.2% |
| R3 | 88.8% |
| R4 | 81.4% |
| R5 | 77.7% |
| R6 | 70.3% |
| R7 | 59.2% |

It is found after experiments that the osteo-implant 100 of this embodiment can combine a bone ingrowth proportion and a surrounding healthy bone proportion, accelerate recovery and reduce surgical failure rates, and then reduce the burden of patients. The improvements of the osteo-implant of the present disclosure in the effect of prompting bone healing as compared with the known art are described in the following with experiment examples.

FIG. 1B is a local sectional view of the osteo-implant of FIG. 1A. Referring to FIG. 1A and FIG. 1B, the fixing segment 110 of the osteo-implant 100 of this embodiment takes a solid design as an example, which may give stronger rigidity to the osteo-implant 100, but the present disclosure is not limited thereto. Referring to FIG. 1A again, the fixing segment 110 of this embodiment has a central axis L12, and the central axis L12 is parallel to the Y axis in FIG. 1A and extends along the axial direction of the columnar body 110A. If the bone healing chamber 114 is sliced by a section parallel to and passing through the central axis L12, it is obtained that contours of multiple sections of the bone healing chamber 114 each have a vertex angle on a side close to the central axis L12. The vertex angle closer to the implant end 120 is greater. For example, when the bone healing chamber 114 is sliced by taking an XY plane as a section through the central axis L12, the contour of the section 114A of the bone healing chamber on the section has a vertex angle A12 on one side close to the central axis L12. Similarly, the section 114B of the bone healing chamber has a vertex angle A22, and the section 114C of the bone healing chamber has a vertex angle A32. The vertex angle A32 of the section 114C of the bone healing chamber is greater than the vertex angle A22 of the section 114B of the bone healing chamber, and the vertex angle A22 of the section 114B of the bone healing chamber is greater than the vertex angle A12 of the section 114A of the bone healing chamber. It is found after experiments that, when the vertex angles of the sections of the bone healing chamber 114 are arranged as above, it is possible to combine the bone ingrowth proportion and the surrounding healthy bone proportion, accelerate recovery and reduce surgical failure rates, and then reduce the burden of patients. In addition, the vertex angle of the section of the bone healing chamber 114 farthest from the implant end 120 is an acute angle, that is, the vertex angle A12 of the section 114A of the bone healing chamber is an acute angle. The vertex angle of the section of the bone healing chamber 114 closest to the implant end 120 is an obtuse angle, that is, the vertex angle A32 of the section 114C of the bone healing chamber is an obtuse angle. In an embodiment, the vertex angle of the section of the bone healing chamber 114 may be between 15° to 160°.

From another perspective, the vertex angle of each section of the bone healing chamber 114 of this embodiment consists of a first edge and a second edge. Multiple angles of the first edges and the central axis L12 decrease in a range of 5° to 45° in a direction from being away from the implant end 120 towards being close to the implant end 120. Multiple angles of the second second edges and the central axis L12 decrease in a range of 5° to 120° in a direction from being away from the implant end 120 towards being close to the implant end 120. Specifically, the vertex angle A12 of the section 114A of the bone healing chamber 114 consists of a first edge E12 and a second edge E14, the vertex angle A22 of the section 114B of the bone healing chamber 114 consists of a first edge E22 and a second edge E24, and the vertex angle A32 of the section 114C of the bone healing chamber 114 consists of a first edge E32 and a second edge E34.

In FIG. 1A, to ease the description about angles between the central axis L12 and two sides of the vertex angle, the central axis L12 is translated to pass through the position of each vertex of vertex angle. In two sides of each vertex angle, one side closer to the positive Y axis direction (i.e., the direction of the central axis L12 away from the implant end 120) is the first edge, and the other side is taken as the second edge. An included angle A14 between the first edge E12 of the vertex angle A12 of the section 114A of the bone healing chamber 114 and the central axis L12 refers to an angle in the case of anticlockwise rotation from the first edge E12 to the central axis L12. An included angle A24 between the first edge E22 of the vertex angle A22 of the section 114B of the bone healing chamber 114 and the central axis L12 refers to an angle in the case of anticlockwise rotation from the first edge E22 to the central axis L12. An included angle A34 between the first edge E32 of the vertex angle A32 of the section 114C of the bone healing chamber 114 and the central axis L12 refers to an angle in the case of anticlockwise rotation from the first edge E32 to the central axis L12. The included angle A14 between the first edge E12 and the central axis L12 is greater than the included angle A24 between the first edge E22 and the central axis L12, and the included angle A24 between the first edge E22 and the central axis L12 is greater than the included angle A34 between the first edge E32 and the central axis L12. In an embodiment, the included angle A14 between the first edge E12 and the central axis L12 is 45°, and the included angle A34 between the first edge E32 and the central axis L12 is 5°. In addition, multiple included angles (including, but not limited to, the included angles A14, A24, and A34) between the first edges (including, but not limited to, the first edges E12, E22 and E32) and the central axis L12 may range from 5° to 45°.

An included angle A16 between the second edge E14 of the vertex angle A12 of the section 114A of the bone healing chamber 114 and the central axis L12 refers to an angle in the case of clockwise rotation from the second sidesecond edge E14 to the central axis L12. An included angle A26 between the second edge E24 of the vertex angle A22 of the section 114B of the bone healing chamber 114 and the central axis L12 refers to an angle in the case of clockwise rotation from the second edge E24 to the central axis L12. An included angle A36 between the second edge E34 of the vertex angle A32 of the section 114C of the bone healing chamber 114 and the central axis L12 refers to an angle in the case of clockwise rotation from the second edge E34 to the central axis L12. The included angle A16 between the second edge E14 and the central axis L12 is greater than the included angle A26 between the second edge E24 and the central axis L12, and the included angle A26 between the second edge E24 and the central axis L12 is greater than the included angle A36 between the second edge E34 and the central axis L12. In an embodiment, the included angle A16 between the second edge E14 and the central axis L12 is 120°, and the included angle A36 between the second edge E34 and the central axis L12 is 15°. In addition, multiple included angles (including, but not limited to, the included angles A16, A26, and A36) between the second edges (including, but not limited to, the second edges E14, E24 and E34) and the central axis L12 may range from 15° to 120°.

The osteo-implant 100 of this embodiment may manufacture an integrally formed structure by an additive manufacturing method, for example, a 3D printing technology, but the present disclosure is not limited thereto.

Figures 2A, 2B:
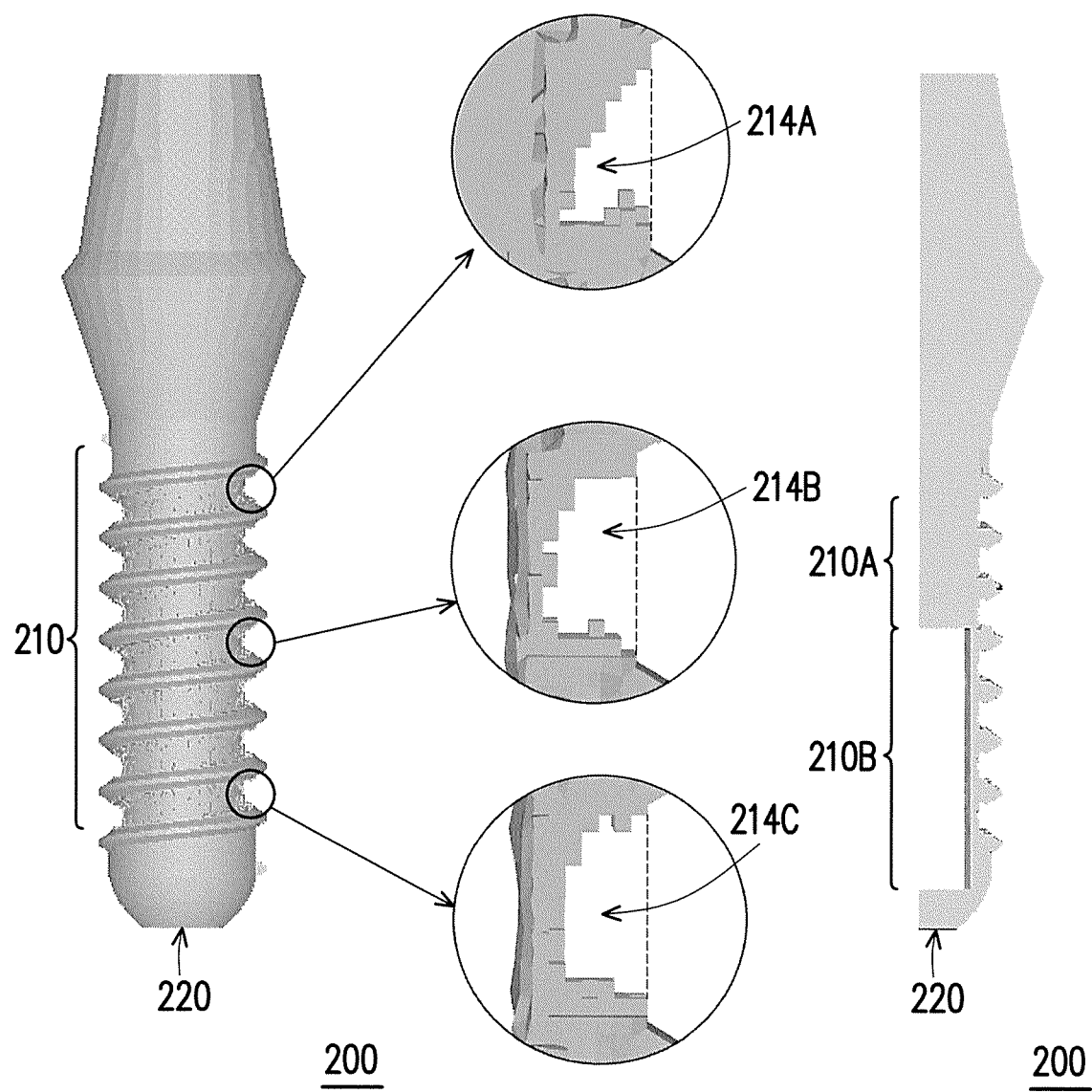
FIG. 2A is a three-dimensional view of an osteo-implant in accordance with an embodiment of the present disclosure and a local section enlarged view thereof.
FIG. 2B is a local sectional view of the osteo-implant of FIG. 2A.

FIG. 2A is a three-dimensional view of an osteo-implant in accordance with an embodiment of the present disclosure and a local section enlarged view thereof, and FIG. 2B is a local sectional view of the osteo-implant of FIG. 2A. Referring to FIG. 2A and FIG. 2B, the fixing segment 210 of the osteo-implant of this embodiment comprises a first segment 210A and a second segment 210B which is located between the first segment 210A and an implant end 220. The first segment 210A is solid and the second segment 210B is hollow. An outer wall of the second segment 210B has a thickness of above 100 μm, which can maintain proper strength. The volume of the hollow part of the second segment 210B, for example, may account for below 60% of the entire volume of the second segment 210B, but the present disclosure is limited thereto. As described in the previous embodiment, in the same segment of the fixing segment 210, the area of the section of the bone healing chamber 114 closer to the implant end 220 is smaller. As shown by the following Table 2, seven sections of the bone healing chamber 214 in FIG. 2A are numbered from being away from the implant end 220 to being closed to the implant end 220, sequentially numbered R1-R7. If the area of the section 214A of the bone healing chamber 214 numbered R1 is 100%, it can be found that the area of the first section 210A of the bone healing chamber 214 of this embodiment is smaller when the section is closer to the implant end 220. In addition, the area of the second section 210B of the bone healing chamber 214 of this embodiment is also smaller when the section is closer to the implant end 220. However, the area of the section of the bone healing chamber 214 which is closest to the implant end 220 in the first segment 210A and numbered R3 is less than the area of the section of the bone healing chamber 214 which is farthest from the implant end 220 in the second segment 210B and numbered R4. In an embodiment, the area of the section of the bone healing chamber 214 numbered R4 is also greater than the area of the section of the bone healing chamber 214 which is farthest from the implant end 220 in the first segment 210A and numbered R1, the hollow second segment 210B may provide an environment suitable for the growth of the bone tissue, so that the area of the section of the bone healing chamber 214 of the second segment 210B is relatively bigger.

TABLE 2

| Section number | Area variation of chamber section |
| --- | --- |
| R1 | 100% |
| R2 | 96.9% |
| R3 | 93.8% |
| R4 | 135.4% |
| R5 | 125.8% |

TABLE 2-continued

| Section number | Area variation of chamber section |
| --- | --- |
| R6 | 109.6% |
| R7 | 102.4% |

FIG. 3A is a three-dimensional view of an osteo-implant in accordance with another embodiment of the present disclosure; FIG. 3B is a local enlarged view of the osteo-implant of FIG. 3A. The osteo-implant 300 of FIG. 3A is similar to the osteo-implant 200 of FIG. 2A, and the similarity is not repeated here. A first segment 310A of the osteo-implant of FIG. 3A is solid, and a second segment 310B of the osteo-implant 300 is hollow and has a central chamber C30 as shown by the dash line. The bone healing chamber 314 is at least partially connected to the central chamber C30, for example, a part of the second segment 310B of the bone healing chamber 314 located in the osteo-implant 300 is in communication with the central chamber C30. In this embodiment, the bone healing chamber 314 of the second segment 310B has multiple pores P30, to be in communication with the central chamber C30. In an embodiment, the section area of a single pore P30 is between 2500 μm2 and 90000 μm2, but the present disclosure is not limited thereto. As shown in the following Table 3, seven sections of the bone healing chamber 314 of FIG. 3A is numbered from being away from the implant end 320 to being close to the implant end 320, sequentially numbered R1-R7. The area of the section of the bone healing chamber 314 numbered R1 is 100%, and it can be found that the area of the section, closer to the implant end 320, of the bone healing chamber 314 of the first segment 310A of the fixing segment 310 of this embodiment is smaller. In addition, the area of the section, closer to the implant end 320, of the bone healing chamber 314 of the second segment 310B of the fixing segment 310 is also smaller. However, the area of the section of the bone healing chamber 314 which is closest to the implant 320 and numbered R3 in the sections of the bone healing chamber 314 of the first segment 310A is smaller than the area of the section of the bone healing chamber 314 which is farthest from the implant 320 and numbered R4 in the sections of the bone healing chamber 314 of the second segment 310B. The design that the bone healing chamber 314 is in communication with the central chamber C30 may increase the bone ingrowth proportion.

TABLE 3

| Section number | Area variation of chamber section |
| --- | --- |
| R1 | 100% |
| R2 | 90.9% |
| R3 | 72.7% |
| R4 | 81.8% |
| R5 | 72.7% |
| R6 | 72.7% |
| R7 | 63.6% |

Figure 4B:
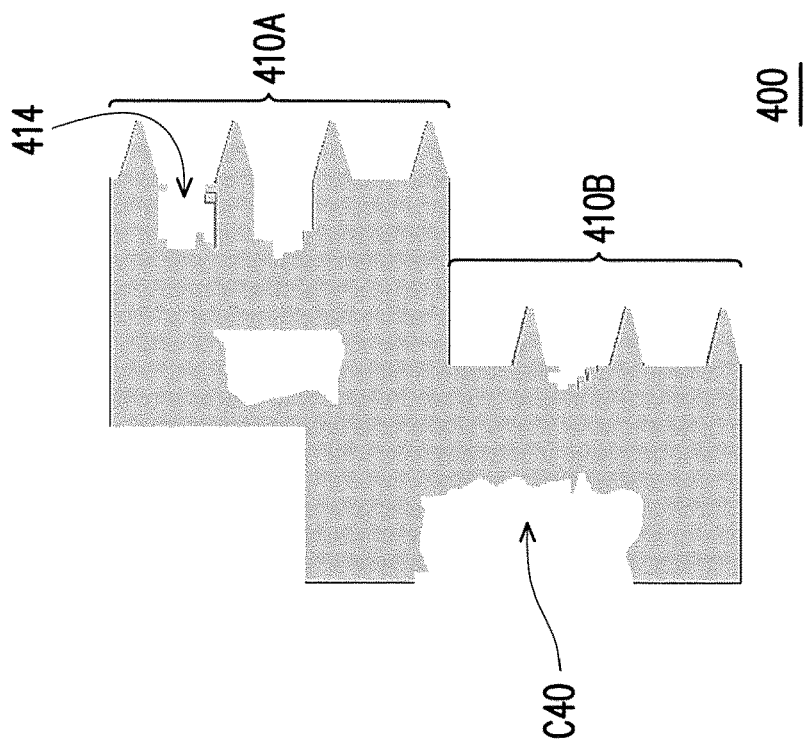
FIG. 4B is a local sectional view of the osteo-implant of FIG. 4A.
Figure 4A:
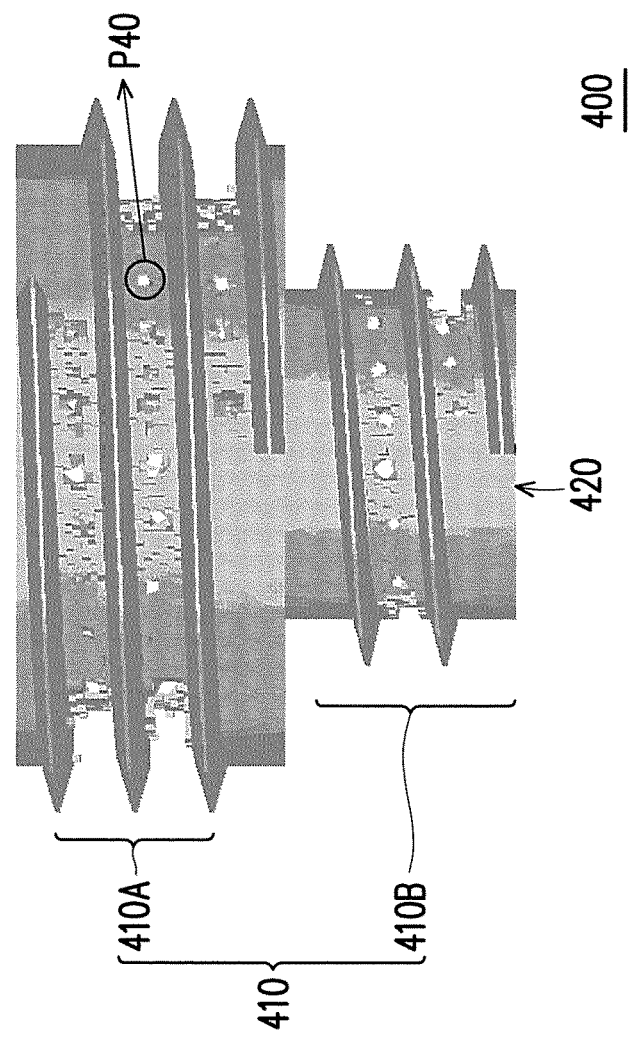
FIG. 4A is a local enlarged view of an osteo-implant in accordance with a yet another embodiment of the present disclosure.

FIG. 4A is a local enlarged view of an osteo-implant in accordance with a yet another embodiment of the present disclosure, and FIG. 4B is a local section view of the osteo-implant of FIG. 4A. The osteo-implant 400 of FIG. 4A is similar to the osteo-implant 300 of FIG. 3A, and the similarity is not repeated here. A fixing segment 410 of the osteo-implant 400 of this embodiment comprises a first segment 410A and a second segment 410B, and the second 410B is located between the first segment 410A and the implant end 420. The first segment 410A and the second segment 410B are both hollow, but the radius of the first segment 410A is different from that of the second segment 410B. In an embodiment, the radius of the second segment 410B is 30%-99% of the radius of the first segment 410A. The areas of the sections of the bone healing chamber 414 still conform to the decreasing rule to gradually decrease from being away from the implant end 420 to being close to the implant end 420, and the lowest layer has hardly any chamber. In addition, a part of the bone healing chamber 414 is in communication with a central chamber C40 via a pore P40.

Figure 6:
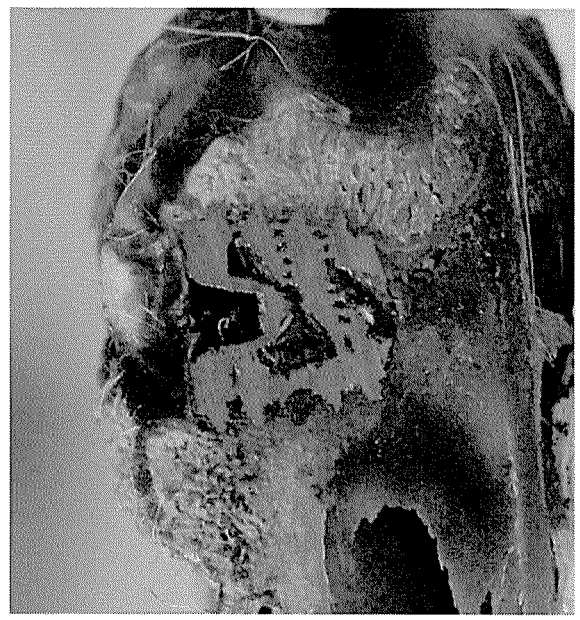
FIG. 5 and FIG. 6 are slice photos of an osteo-implant after an animal test in accordance with an embodiment of the present disclosure.
Figure 5:
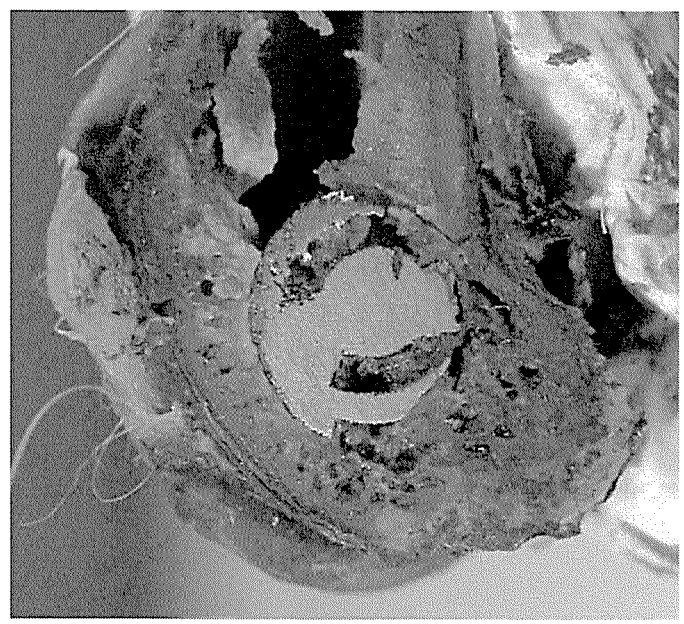

FIG. 5 and FIG. 6 are slice photos of an osteo-implant after an animal test in accordance with an embodiment of the present disclosure. The design of the osteo-implant of FIG. 5 and FIG. 6 is substantially similar to that of the osteo-implant of FIG. 4A. The inventor implants an osteo-implant of an experiment example of the present disclosure into an animal body, and observes a situation where the osteo-implant prompts generation of bone tissues. In the first month, traces of new bones are attached to the surface of the osteo-implant of this embodiment, and meanwhile, traces of bones enter the central chamber. In the second month, it is visible that the new bones grow around the osteo-implant and in the bone healing chamber, to increase stability thereof, as the horizontal section of FIG. 5 and the vertical section of FIG. 6. The interior and the surface of the osteo-implant of this embodiment are both covered by new bones, and new bone tissues fit closely to the surface of the osteo-implant. In one month of the implant, the bone mass density (BMD) of the conventional osteo-implant is 0.88±0.48, while the BMD of the osteo-implant of the experiment example can reach 1.14±0.48. The bone volume ratio (BV/TV) of the conventional osteo-implant is about 66.79%, while the BV/TV of the osteo-implant of the experiment example can reach 85.15%. The bone surface density of the conventional osteo-implant is about 6.47/unit area, while the bone surface density of the osteo-implant of the experiment example can reach 7.25/unit area. In addition, the performance of the experiment that uses the osteo-implant of the experiment example in a torsion test after two-month implant is superior to the experiment that uses the conventional osteo-implant. Thus, it can prove that the osteo-implant of the present disclosure has a good bone healing rate.

The osteo-implants of the above embodiments are applied to gums, but the present disclosure is not limited thereto.

Figure 7:
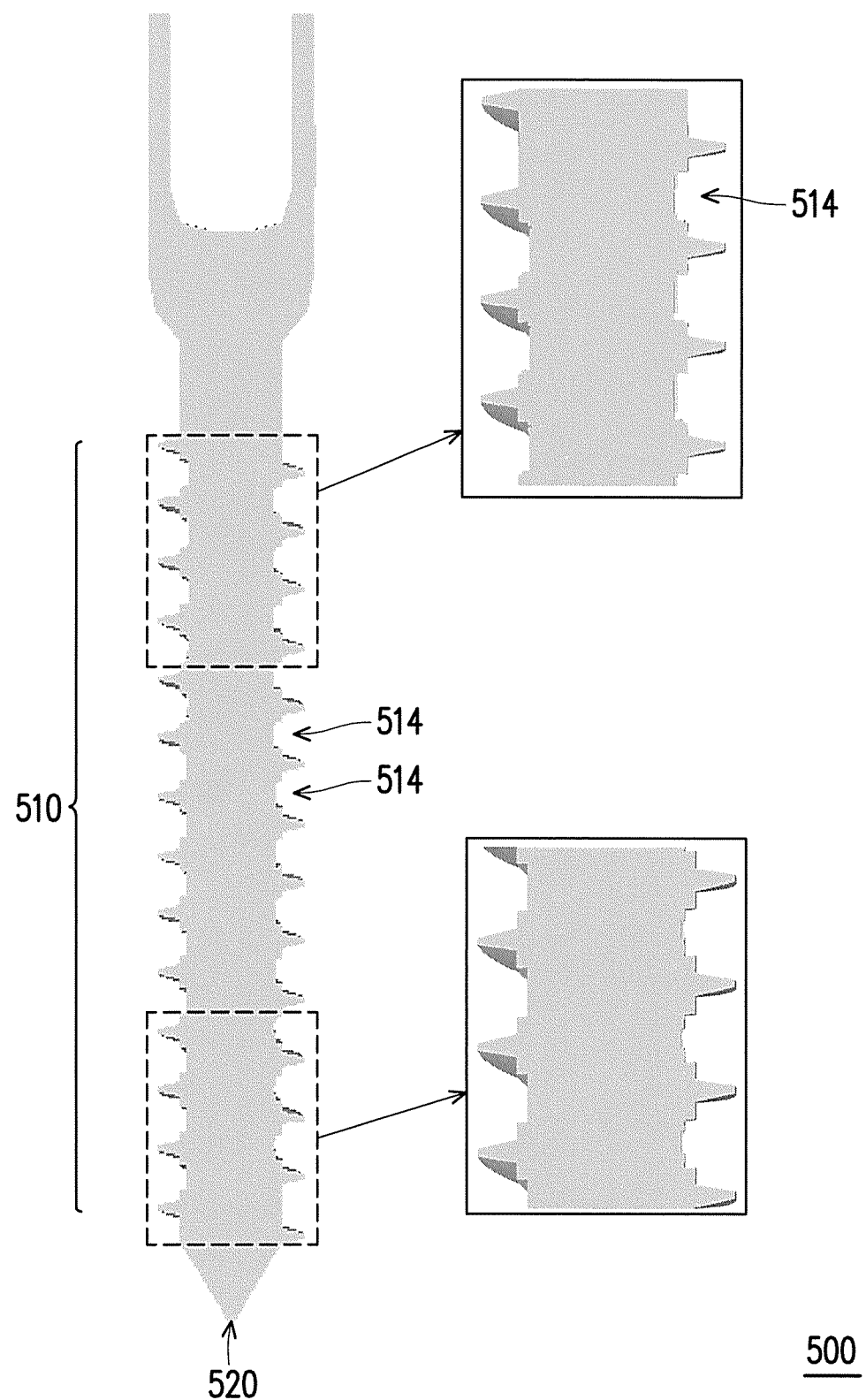
FIG. 7 is a three-dimensional view of an osteo-implant in accordance with another embodiment of the present disclosure and a local section enlarged view thereof.

FIG. 7 is a three-dimensional view of an osteo-implant in accordance with another embodiment of the present disclosure and a local section enlarged view thereof. Referring to FIG. 7, the osteo-implant 500 of this embodiment is similar to the osteo-implant 100 of FIG. 1A, and the similarities are not repeated herein. The osteo-implant 500 of FIG. 7 is applied to pedicle screw fixation, and areas of sections of a bone healing chamber 514 of a fixing segment 510 are also smaller when the sections are closer to an implant end 520. As shown by the following Table 4, thirteen sections of the bone healing chamber 514 in FIG. 7 are numbered from being away from the implant end 520 to being close to the implant end 520, sequentially numbered R1-R13. If the area of the section of the bone healing chamber 514 numbered R1 is 100%, it can be found that the areas of the sections of the bone healing chamber 514 are smaller when the sections are closer to the implant end 520.

TABLE 4

| Section number | Area variation of chamber section |
| --- | --- |
| R1 | 100% |
| R2 | 71.6% |
| R3 | 71.6% |
| R4 | 65.0% |
| R5 | 65.0% |
| R6 | 61.6% |
| R7 | 61.6% |
| R8 | 61.6% |
| R9 | 76.6% |
| R10 | 76.6% |
| R11 | 78.3% |
| R12 | 78.3% |
| R13 | 65.0% |

Figure 8:
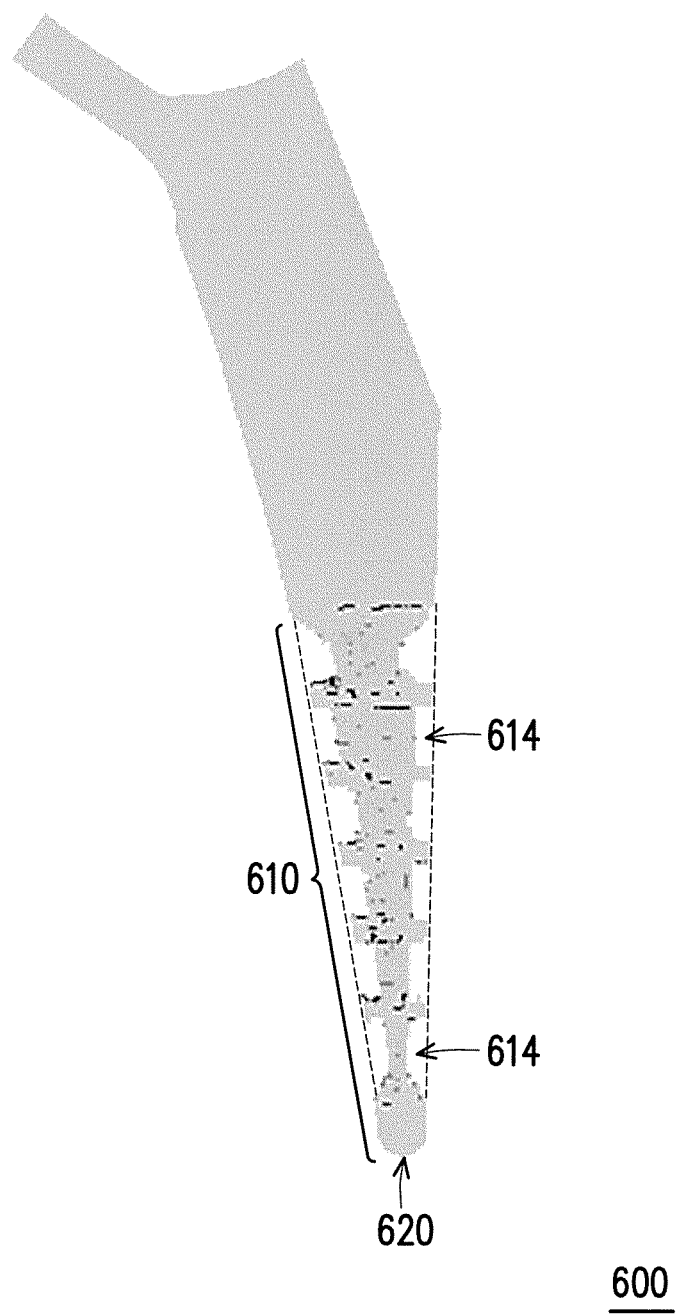
FIG. 8 is a three-dimensional view of an osteo-implant in accordance with a yet another embodiment of the present disclosure and a local section enlarged view thereof.

FIG. 8 is a three-dimensional view of an osteo-implant in accordance with a yet another embodiment of the present disclosure and a local section enlarged view thereof. Referring to FIG. 8, the osteo-implant 600 of this embodiment is similar to the osteo-implant 100 of FIG. 1A, and the similarities are not repeated herein. The osteo-implant 600 of FIG. 8 is applied to hip joints, and threads of a fixing segment 610 are multiple closed ring-like ridge structures around the surface of the fixing segment 610, enabling the fixing segment 610 to have multiple bone healing chambers 614. The closer sections of the multiple bone healing chambers 614 are to the implant end 620, the smaller the areas thereof are. In FIG. 8, the original position of the surface 116 of the columnar body of the fixing segment 610 is indicated with dotted lines, chambers inwardly depressed towards the interior of the osteo-implant 600 from the position indicated with dotted lines are bone healing chambers 614, and areas of sections of the multiple bone healing chambers 614 are also calculated according to the rule. As shown by the following Table 5, six bone healing chambers 614 in FIG. 8 are numbered from being away from the implant end 620 to being close to the implant end 620, sequentially numbered R1-R6. If the area of the section of the bone healing chambers 614 numbered R1 is 100%, it can be found that the areas of the sections of the bone healing chambers 614 are smaller when the sections are closer to the implant end 620.

TABLE 5

| Section number | Area variation of chamber section |
| --- | --- |
| R1 | 100% |
| R2 | 98.6% |
| R3 | 44.4% |
| R4 | 29.6% |
| R5 | 23.6% |
| R6 | 5.7% |

In summary, the osteo-implant of the present disclosure has at least one bone healing chamber at a thread root, and areas of sections of the bone healing chambers on the same section gradually decrease towards the implant end. Such a design not only can adjust overall rigidity of the osteo-implant, but also increases the bone integration ratio and accelerates the bone healing speed.

Although the present disclosure has been disclosed as above with embodiments, the embodiments are not used to limit the present disclosure. Any person of ordinary skill in the art can make some changes and modifications without departing from the spirit and scope of the present disclosure, and thus the protection scope of the present disclosure is as defined by the appended claims.

What is claimed is:

1. An osteo-implant, having a fixing segment and an implant end, wherein the fixing segment is provided with a thread and at least one bone healing indentation, the at least one bone healing indentation is located at a thread root of the thread, the at least one bone healing indentation is an indentation inwardly depressed from a surface of the fixing segment, the fixing segment has a central axis, and in a part of ef-the fixing segment, an area of at least one section of the at least one bone healing indentation that is closer to the implant end is smaller than an area of a different section of the at least one bone healing indentation that is farther from the implant end, the sections are parallel to and passes through the central axis, wherein contours of multiple sections of the at least one bone healing indentation each have a first edge, a second edge, and a vertex angle formed by the first edge and the second edge on one side closer to the central axis, and the vertex angle of one of the contours of the multiple sections closer to the implant end is greater than the vertex angle of another one of the contours of the multiple sections that is farther from the implant end, the multiple sections are parallel to and pass through the central axis, wherein the fixing segment comprises a first segment and a second segment, the second segment is between the first segment and the implant end, the first segment is solid, and the second segment is hollow, an outer wall of the second segment has a thickness of above 100 µm.

2. The osteo-implant of claim 1, wherein the vertex angle farthest from the implant end is an acute angle, and the vertex angle closest to the implant end is an obtuse angle.

3. The osteo-implant of claim 1, wherein the first edge is closer to the central axis than the second edge, and multiple included angles formed by the first edges and the central axis decrease in a direction away from the implant end to being close to the implant end.

4. The osteo-implant of claim 3, wherein the included angles each range from 5° to 45°.

5. The osteo-implant of claim 1, wherein the first edge is closer to the central axis than the second edge, and multiple included angles formed by the second edges and the central axis decrease in a direction away from the implant end to being close to the implant end.

6. The osteo-implant of claim 5, wherein the included angles each range from 15° to 120°.

7. The osteo-implant of claim 1, wherein the radius of the second segment is 30% to 99% of the radius of the first segment.

8. The osteo-implant of claim 1, wherein in the first segment, an area of a section of the at least one bone healing indentation closer to the implant end is smaller than an area of a different section of the at least one bone healing indentation that is farther from the implant end, the sections are parallel to and pass through the central axis, and, in the second segment, an area of a section of the at least one bone healing indentation closer to the implant end is smaller than an area of a different section of the at least one bone healing indentation that is farther from the implant end, the sections are parallel to and pass through the central axis.

9. The osteo-implant of claim 8, wherein an area of a section of the at least one bone healing indentation closest to the implant end is smaller than that of a section of the at least one bone healing indentation farthest from the implant end.

10. The osteo-implant of claim 1, wherein the fixing segment is hollow and has a central chamber, and the at least one bone healing indentation is at least partially communicated with the central chamber.

11. The osteo-implant of claim 10, wherein the at least bone healing indentation has muptiple pores, to be communicated with the central indentation, and the section area of each of the pores is between 2500 $\mu m^2$ and 90000 $\mu m^2$.

* * * * *